United States Patent [19]

Sawaragi et al.

[11] Patent Number: 4,888,434

[45] Date of Patent: * Dec. 19, 1989

[54] ANTIMICROBIAL AGENT

[75] Inventors: Fujio Sawaragi, Chigasaki; Hiroo Taniguchi, Hadano, both of Japan

[73] Assignee: Dow Corning K.K., Tokyo, Japan

[*] Notice: The portion of the term of this patent subsequent to Sep. 12, 2006 has been disclaimed.

[21] Appl. No.: 197,778

[22] Filed: May 23, 1988

[30] Foreign Application Priority Data

May 26, 1987 [JP] Japan .................................. 62-127057

[51] Int. Cl.$^4$ .............................................. C07F 7/10
[52] U.S. Cl. .................................................. 556/418
[58] Field of Search ................ 556/418, 424, 420, 413

[56] References Cited

U.S. PATENT DOCUMENTS

| | | | |
|---|---|---|---|
| 3,494,951 | 2/1970 | Belger | 556/420 |
| 3,716,569 | 2/1973 | Redmore et al. | 556/418 |
| 4,005,117 | 1/1977 | Heckert et al. | 556/418 |
| 4,088,670 | 5/1978 | Borgain et al. | 556/420 |
| 4,209,455 | 6/1980 | Pepe | 556/424 |
| 4,472,566 | 9/1984 | Ziemelis et al. | 556/424 |

FOREIGN PATENT DOCUMENTS 0114399 8/1984 European Pat. Off. ............ 556/420

Primary Examiner—John Doll
Assistant Examiner—Stuart L. Hendrickson
Attorney, Agent, or Firm—Jim L. DeCesare

[57] ABSTRACT

An antimicrobial agent which is a carboxyl group containing amine compound. The compound has the characteristics of an amphoteric surfactant and is silyl group containing. The compound is prepared by reacting an amine, a silane, and a carboxylic acid.

11 Claims, No Drawings

ANTIMICROBIAL AGENT

BACKGROUND OF THE INVENTION

The present invention relates to a silyl group-containing compound, and more specifically, relates to an antimicrobial agent comprising a silyl group-containing amphoteric surfactant.

Amphoteric surfactants offer the advantage of broad antimicrobial spectra, and are thus widely used, for example, for disinfecting and washing hands, instruments, and sickrooms, in the medical sphere; for disinfecting and washing facilities, bottles, cans, and vats, in the food processing and fermentation industries; and for disinfecting and washing equipment and sheds in the dairy industry.

However, although antimicrobial agents which consist of amphoteric surfactants do have an excellent antimicrobial effect in washing and disinfecting procedures, they nevertheless suffer from a durable adhesion. Thus, when the antimicrobial agent is continuously exposed to water, it is removed from the substrate material, with the result that the antimicrobial activity falls off substantially within a short period of time.

SUMMARY OF THE INVENTION

The object of the present invention is the resolution of the aforementioned problem encountered with antimicrobial agents comprising amphoteric surfactants, by means of introduction of an antimicrobial agent whose adhesion to the substrate material is durable, and which continues to manifest its initial antimicrobial activity for long periods of time even when repeatedly washed or continuously exposed to water.

The antimicrobial agent of the present invention consists of a silyl group-containing compound having the formula:

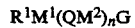

wherein
$R^1$ is a hydrophobic monovalent hydrocarbon group;
Q is an alkylene group having 1 to 7 carbon atoms or the phenylene group;
$M^1$ and $M^2$, are the same or differ, and are selected from the group consisting of the following radicals:

 formula (i)

 formula (ii)

 formula (iii)

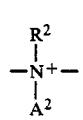 formula (iv)

 formula (v)

 formula (vi)

wherein $R^2$ is the hydrogen atom or R and R is alkyl having no more than 4 carbons or the phenyl group, $A^1$ is a group having —ZCOOH in which Z is alkylene or a substituted alkylene radical, $A^2$ is a group having —ZCOO— in which Z is as defined above, and $A^3$ is a group having —Y—SiR$^3_a$(OR$^4$)$_{3-a}$ in which Y is a divalent hydrocarbon radical of one to eight carbon atoms which contain —COO— or —O— radicals or cyclic structures; $R^3$ is an alkyl group; $R^4$ is an alkyl group or acyl group; and a is 0, 1 or 2.

G is $R^2$, $A^1$, $A^2$, or $A^3$ wherein $R^2$, $A^1$, $A^2$, and $A^3$ are defined as above; and n is zero or an integer having a value of 1 through 4; and wherein at least one group of $A^1$ or $A^2$ and at least one group of $A^3$ are present in the molecule, with the proviso that the formula (vi) group is always present together with the formula (iii) group. $A^1$ may also be a group containing —COOH.HX where X is halogen. The nitrogen atom present in the molecule may form a salt together with hydrogen halide. $A^1$ may also be a group containing —COOH.

DETAILED DESCRIPTION OF THE INVENTION

The antimicrobial agent of the present invention, is a carboxyl group-containing amine compound and has the characteristics of an amphoteric surfactant. It thus has an excellent antimicrobial activity, and, while it adheres to the substrate by physical adhesion, being a silyl group-containing compound it also adheres through chemical bonding via the silyl group. The antimicrobial activity is thus maintained for long periods of time as a consequence of the high durability generated by this adhesion.

The antimicrobial agent of the present invention can be prepared by reacting an amine compound having the formula (1) with a silane compound having formula (2) and a carboxylic acid having formula (3).

The Amine Compound (1)

Compounds having the following formula:

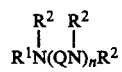 (1)

are used as the amine compound. $R^1$ is a hydrophobic monovalent hydrocarbon group, as exemplified by alkyl groups having 4 to 20 carbon atoms (for example, butyl, octyl, lauryl); aryl groups; aralkyl groups (for example, benzyl, chlorobenzyl, phenylbenzyl, diphenylmethyl); polyoxyalkylene (preferred examples consist of polyoxypropylene); and compounds having the formula:

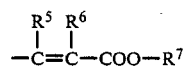

In the above formula, $R^5$ and $R^6$ are each the hydrogen atom or alkyl group having 1 through 20 carbon atoms, aryl groups, aralkyl groups, and polyoxyalkylene, and $R^7$ = alkyl groups having 1 through 20 carbon atoms, aryl groups, aralkyl groups, and polyoxyalkylene.

Furthermore, one of the three groups $R^2$ in formula (1) must be a hydrogen atom, while the other two groups $R^2$, which may be the same or may differ, represent the hydrogen atom, alkyl groups having up to four carbon atoms (for example, methyl, ethyl, propyl), and phenyl.

In addition, Q is phenylene or an alkylene group having one through seven carbon atoms, and n is zero or an integer with a value of one through four.

The amine compound (1) can be prepared by the reaction of a halide, epoxy compound, an acrylate, or methacrylate, corresponding to group $R^1$, with a compound having the formula:

Also, various alkylamino compounds having 8 through 18 carbons and the compound with the formula:

are available.

Preferred amine compounds (1) are obtained by the reaction of alkyleneamine, for example, diethylenetriamine, with compounds having the following formulas:

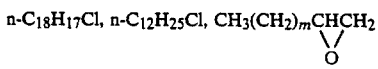

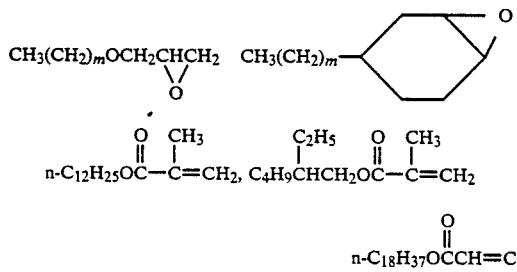

These reactions can be conducted, for example, by the addition of excess alkyleneamine and heating at approximately 180 degrees Centigrade.

Examples of the amine compound (1) are as follows:

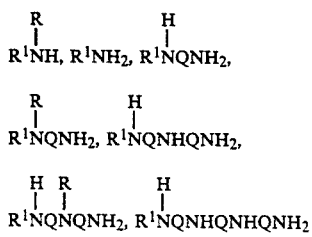

In each of the above formulas, R is an alkyl group having up to four carbons or the phenyl group, $R^1$ and Q are defined as above, although —$CH_2CH_2$— and —$CH_2CH_2CH_2$— are preferred for Q.

The hydrophobic group $R^1$ in amine compound (1) provides an affinity for bacterial surfaces, which thus sets up the conditions for the generation of antimicrobial activity.

The Silane Compound

The aforementioned silane is a silane compound having a functional group capable of reacting with the amino or imino moiety in the amine compound (1) described above, and the silane has the formula:

$$Y^1SiR^3{}_a(OR^4)_{3-a} \qquad (2)$$

Here, $Y^1$ is a functional group which can react with the amino group (—$NH_2$) or imino group (>NH), and examples thereof are:

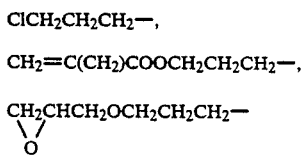

$R^3$ is an alkyl group having one through four carbons, $R^4$ is an alkyl group or acyl group having one through four carbons, and a is an integer having a value of zero through two. Preferred examples are: —$Si(OCH_3)_3$, —$SiCH_3(OCH_3)_2$, and —$Si(OCH_2CH_3)_3$.

The Functionalized Carboxylic Acid

The functionalized carboxylic acid contains a functional group which will react with the primary, secondary, or tertiary nitrogen atoms present in amine compound (1), and it has the formula:

$$Z^1\text{—COOH} \qquad (3)$$

$Z^1$ represents the aforementioned functional group. Examples of carboxylic acid (3) are, for example, carboxylic acid compounds having the formula:

$$X\text{—}R^8\text{—COOH}$$

In the above formula, X—$R^8$ is a haloalkyl group, haloallyl group, haloaryl group, or haloaralkyl group, with the halogen being Cl or Br, as well as alpha, beta-unsaturated carboxylic acids, and epoxy-containing alkylcarboxylic acids. Examples are:

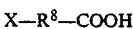

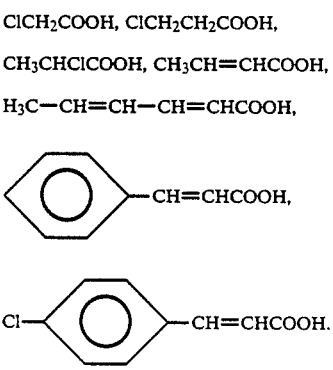

Furthermore, the functionalized carboxylic acid can be used as its alkyl ester, although after the reaction, a hydrolytic de-esterification must be carried out.

The amine compound (1) is first reacted with either the silane compound (2) or the functionalized carboxylic acid (3), and the nitrogen in the reaction product is reacted with the other of the silane compound (2) and the functionalized carboxylic acid (3). It is preferred that the amine compound (1) be reacted first with the silane compound (2), and that the reaction product therefrom be reacted with the functionalized carboxylic acid (3).

The proportions of amine compound (1), silane compound (2), and functionalized carboxylic acid (3) will vary; however, an excess of silane compound (2) from a 1:1:1 molar ratio, for example, up to about 1.5-fold, is preferred.

Preferred examples of the antimicrobial agents of the present invention are as follows:

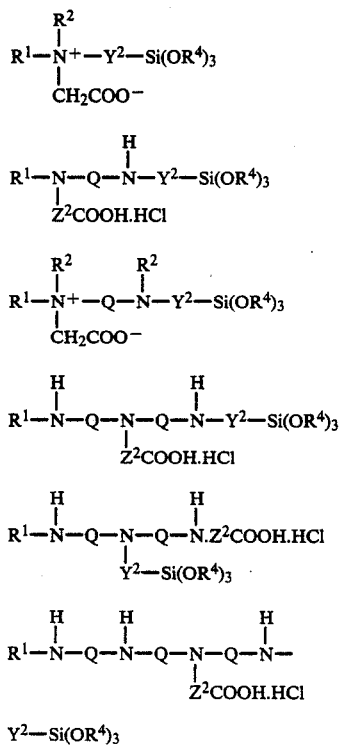

In the preceding, $Y^2$ represents the residue from the reaction of $Y^1$ in silane compound (2) with an amino or imino group, and $Z^2$ is the residue from the reaction of $Z^1$ in functionalized carboxylic acid (3) with an amino or imino group.

In each formula, it is preferred that Q be $-CH_2CH_2-$ or $-CH_2CH_2CH_2-$.

The following are preferred for $Y^2$:

$$-CH_2CH_2CH_2-,$$

$$-CH_2\underset{\underset{CH_3}{|}}{C}HCOOCH_2CH_2CH_2-$$

$$-CH_2-\underset{\underset{OH}{|}}{C}HCH_2OCH_2CH_2CH_2-$$

The following are preferred for $Z^2$:

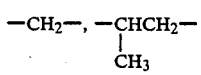

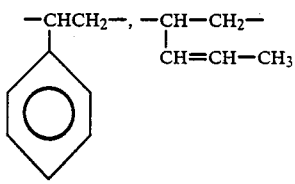

The antimicrobial agent of the present invention can be used by treatment of the surface of a solid or by mixing into the surface of the solid. In its practical application, the antimicrobial agent can be mixed with other bases, diluents, viscosity regulators, and other ingredients.

For example, the antimicrobial agent can be dissolved or dispersed in water, alcohols, or other hydrophilic organic solvents, or in hydrophobic organic solvents, in order to prepare a treatment or coating liquid. Also, alkali metal hydroxides, amine compounds, gamma-aminopropylsilanes, for example, N-(2-aminoethyl)-3-aminopropylsilane, fatty acid metal salts, alkali metal acetates, metal acetonates, alkyl titanates and polymers, and alkyl silicates such as sodium silicate and polymers can be added in order to accelerate chemical adhesion by the silyl group. It is also possible to use mineral acids and organic acids.

Additionally, the antimicrobial agent of the present invention can be applied by dispersing it in a paint base prepared from synthetic resins or emulsions and by applying it on solid surfaces.

As noted above, the antimicrobial agent of the present invention is a silyl group-containing compound having the characteristics of a carboxylic acid-type amphoteric surfactant. In consequence, it has antimicrobial activity against gram-positive bacteria, gram-negative bacteria, molds, algae, and yeast, an antimicrobial activity against bacteria as well as an antimold activity and an algae-controlling activity. At the same time, chemical adhesion is obtained, through the silyl group, for solids to which it is applied. The result is substantial durability and long-term maintenance of the antimicrobial activity. For example, as will be understood from the examples given below, the antimicrobial agent, when applied to fabrics, has resistance to washing.

The antimicrobial activity is thought to arise from the intramolecular generation of a quaternary ammonium salt by dissociation of the $-COOH$ or $-COOH\cdot HCl$ group from the functionalized carboxylic acid (3) resulting in $-COO-$ or $-COOH\cdot Cl-$ together with the development of $N^+$ at the amino or imino moiety from amine compound (1). This quaternary ammonium salt contributes to metabolic abnormalities in the microorganism and thus kills the microorganism.

The present invention will be explained with reference to illustrative examples, but the present invention is not limited to these examples.

The high-performance liquid chromatography used in the examples was carried out with a Shim-pack PREP-ODS (2×25 cm) column and the solvent was methanol.

EXAMPLE 1

Synthesis of the Amine Compound

4 Moles diethylenetriamine was placed in a four-neck flask and heated to 180 degrees Centigrade with stirring under a nitrogen current. To this was added dropwise 1 mol n-octyl chloride over 3.5 hours. After cooling, the diethylenetriamine hydrochloride product was filtered off. Distilling the transparent light-yellow liquid in vacuum at 123 to 135 degrees Centigrade and 1.5 mmHg afforded 200 g of a transparent, colorless fraction (1) (yield=93%).

Fraction (1) was an amine compound with the chemical structure:

$$CH_3(CH_2)_7NHCH_2CH_2NHCH_2CH_2NH_2$$

Preparation of Antimicrobial Agent 1

5.4 g of fraction (1) prepared above and 5.4 g of a methanol solution containing 40% crotonic acid were sealed in a glass ampula and heated at 90 degrees Centigrade for 1 hour to produce a transparent yellow liquid. 5.5 g gamma-chloropropyltrimethoxysilane was added to this liquid, and this was sealed in a tube and heated at 120 degrees Centigrade for 8 hours, to produce a viscous, transparent, and brown liquid. This liquid was subjected to high-performance liquid chromatography, and the peak with a retention time of 19.11 minutes was collected to afford antimicrobial agent 1 of the present invention, which had the chemical structure:

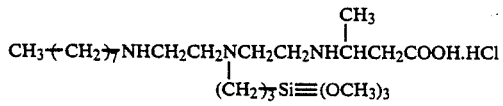

EXAMPLE 2

Preparation of Antimicrobial Agent 2

5.0 g fraction (1) as described above, 5.1 g gamma-chloropropyltrimethoxysilane, and 4.3 g methanol were sealed in a glass ampula and heated at 120 degrees Centigrade for 12 hours afforded a transparent yellow solution. After cooling, 9.3 g 10% methanolic sodium hydroxide and 14 g molecular sieve 3A manufactured by Union Showa Kabushiki Kaisha were added, followed by stirring for 4 hours. The molecular sieve 3A and sodium chloride product were filtered, the filtrate concentrated to a nonvolatiles concentration of 90%, and the precipitated solid filtered.

The filtrate was diluted with methanol to a nonvolatiles concentrated of 45%, and 4.7 g of solution and 2.4 g of a methanol solution containing 50% monochloroacetic acid were sealed in a glass ampula and heated at 90 degrees Centigrade for 30 minutes to afford a transparent yellow solution. This liquid was subjected to high-performance liquid chromatography, and the peak having a retention time of 17.5 minutes was collected to afford antimicrobial agent 2 of the present invention, which had the chemical structure:

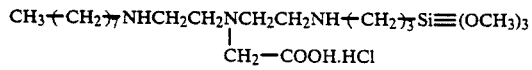

EXAMPLE 3

Synthesis of the Amine Compound

Triethylenetetramine and n-octyl chloride were reacted using the molar ratio and reaction conditions described in Example 1. After filtering the solids, the filtrate was distilled in vacuum at 1.5 mmHg and 169 to 171 degrees Centigrade to afford a transparent and colorless fraction (2).

Fraction (2) was an amine compound having the chemical structure:

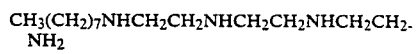

$$CH_3(CH_2)_7NHCH_2CH_2NHCH_2CH_2NHCH_2CH_2NH_2$$

Preparation of Antimicrobial Agent 3

4.0 g of fraction (2) prepared above, 4.2 g gamma-methacryloxypropyltrimethoxysilane, and 1.7 g methanol were sealed in a glass ampula and heated at 120 degrees Centigrade for 12 hours to produce a transparent brown solution.

2.9 g of a methanol solution containing 50% monochloroacetic acid was added to this solution, and sealed in a tube and heated at 90 degrees Centigrade for 10 minutes to produce a viscous, brown, and transparent liquid. This solution was subjected to high-performance liquid chromatography, and the peak with a retention time of 21.5 minutes was collected to afford antimicrobial agent 3 of the present invention, which had the chemical structures:

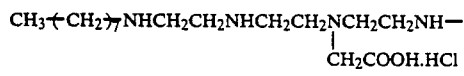

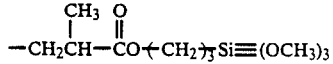

and

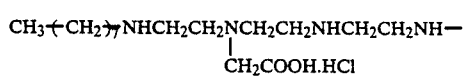

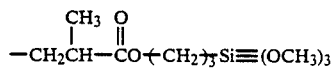

EXAMPLE 4

Preparation of Antimicrobial Agent 4

5.0 g of fraction (2) above, 4.2 g gamma-chloropropyltrimethoxysilane, and 4.0 g methanol were sealed in a glass ampula and heated at 120 degrees Centigrade for 12 hours to afford a transparent yellow solution.

This solution was combined with 7.8 g 10% methanolic sodium hydroxide and 11.6 g molecular sieve 3A and stirred for 4 hours. The molecular sieve 3A and sodium chloride product were filtered, the filtrate was concentrated to a nonvolatiles concentration of 90%, and the precipitated solid was filtered.

The filtrate was diluted with methanol to a nonvolatiles concentration of 32.5%, and 12.0 g of solution and 1.75 g of a methanol solution containing 50% monochloroacetic acid were sealed in a glass ampula and heated at 90 degrees Centigrade for 30 minutes to produce a transparent yellow solution. This liquid was subjected to high-performance liquid chromatography, and the peak with a retention time of 19.15 minutes was collected to afford antimicrobial agent 4 of the present invention, which had the chemical structures:

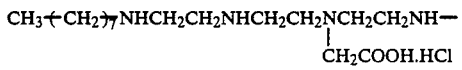

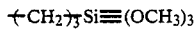

and

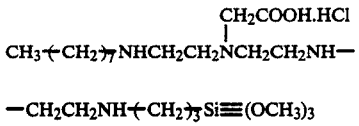

Example 5

Synthesis of the Amine Compound

Diethylenetriamine and n-lauryl chloride were reacted using the molar ratio and reaction conditions of Example 1. After filtering the solids, the filtrate was distilled in vacuum at 2.0 mmHg and 168 to 169 degrees Centigrade to produce a transparent, colorless fraction (3).

Fraction (3) was an amine compound with the chemical structure:

$$CH_3(CH_2)_{11}NHCH_2CH_2NHCH_2CH_2NH_2$$

Preparation of Antimicrobial Agent 5

5.0 g of fraction (3) above, 4.0 g gamma-chloropropyltrimethoxysilane, and 4.0 g methanol were sealed in a glass ampula and heated at 120 degrees Centigrade for 12 hours to prepare a transparent yellow solution.

After cooling, 7.4 g 10% methanolic sodium hydroxide and 11.1 g molecular sieve 3A were added to this solution, followed by stirring for 4 hours. The molecular sieve 3A and sodium chloride product were filtered, the filtrate was concentrated to a nonvolatiles concentration of 90%, and the precipitated solid was filtered.

The filtrate was diluted with methanol to a nonvolatiles concentration of 32.7%, and 12 g of solution and 1.7 g of a methanol solution containing 50% monochloroacetic acid were sealed in a glass ampula and heated at 90 degrees Centigrade for 30 minutes to produce a transparent yellow solution. This solution was subjected to high-performance liquid chromatography, and the peak with a retention time of 19.32 minutes was collected to afford antimicrobial agent 5 of the present invention, which had the chemical structure:

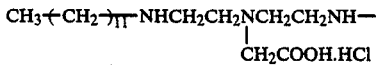

EXAMPLE 6

Synthesis of the Amine Compound

Iminobispropylamine and n-octyl chloride were reacted using the molar ratio and reaction conditions described in Example 1. After filtering the solids, the filtrate was distilled in vacuum at 1.5 mmHg and 135 to 137 degrees Centigrade to obtain a transparent and colorless fraction (4).

Fraction (4) was an amine compound having the chemical structure:

$$CH_3(CH_2)_7NHCH_2CH_2CH_2NHCH_2CH_2CH_2NH_2$$

Preparation of Antimicrobial Agent 6

5.0 g of the fraction (4) above, 4.5 g gamma-chloropropyltrimethoxysilane, and 4.0 g methanol were sealed in a glass ampula and heated at 120 degrees Centigrade for 12 hours to produce a transparent yellow solution.

8.2 g 10% methanolic sodium hydroxide and 12.4 g molecular sieve 3A were added to this solution, following by stirring for 4 hours. The molecular sieve 3A and sodium chloride product were then filtered, the filtrate was concentrated to a nonvolatiles concentration of 90%, and the precipitated solid was filtered.

The filtrate was diluted with methanol to a nonvolatiles concentration of 35.2%, and 11 g of solution and 1.8 g of a methanol solution containing 50% monochloroacetic acid were sealed in a glass ampula and heated at 90 degrees Centigrade for 30 minutes to produce a transparent brown solution. This solution was subjected to high-performance liquid chromatography, and the peak with a retention time of 21.32 minutes was collected to afford antimicrobial agent 6 of the present invention, which had the chemical structure:

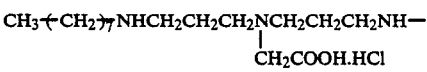

In the following examples, the amount refers to the quantity of active component, and in each case, drying was conducted at 70 degrees Centigrade for 30 minutes.

EXAMPLE 7

Using the antimicrobial agents 1, 4, and 6 described above, treatment baths were prepared as 1.0 owf % (owf %=weight percentage of antimicrobial agent based on the unit weight of raw test fabric) aqueous solutions of the antimicrobial agent. Using a pad-dyeing machine, raw fabric for dye testing cotton jersey was treated with each treatment bath.

EXAMPLE 8

As in Example 7, treatment baths were produced from antimicrobial agents 2 and 5 using a water and ethanol mixture (2:8) to prepare 1.0 owf % antimicrobial agent solutions. Raw fabric for dye testing cotton jersey was treated with each treatment bath as in Example 7.

EXAMPLE 9

In the place of the antimicrobial agent of the present invention, lauryldi(aminoethyl)glycine manufactured as Anon LG from Nippon Yushi Kabushiki Kaisha, a carboxylic acid-type amphoteric surfactant but without an alkoxysilyl group, was used to treat raw fabric for dye testing cotton jersey according to Example 7.

EXAMPLE 10

Using antimicrobial agent 3, an aqueous 1.0 owf % antimicrobial agent solution with a pH of 7 was prepared as in Example 7. A treatment bath was prepared by adjusting the pH of aqueous solution to 8 by the addition of 10% aqueous sodium hydroxide. Raw fabric for dye testing cotton jersey was treated using the treatment bath as in Example 7.

EXAMPLE 11

A 1.0 owf % aqueous solution of antimicrobial agent was prepared as in Example 7 using antimicrobial agent 3. A treatment bath was prepared by the addition to aqueous solution of N-(2-aminoethyl)-3-aminopropylsilane to a concentration of 10.44 owf %. Raw fabric for dye testing cotton jersey was treated as in Example 7 using the treatment bath.

EXAMPLE 12

With antimicrobial agents 3 and 4, treatment baths were produced by preparing 1.0 owf % aqueous solutions of antimicrobial agent as in Example 7. These treatment baths were used to treat raw fabric for dye testing polyester jersey as in Example 7.

EXAMPLE 13

In place of the antimicrobial agent of the present invention, lauryldi(aminoethyl)glycine, Anon LG from Nippon Yushi Kabushiki Kaisha, a carboxylic acid-type amphoteric surfactant without an alkoxysilyl group, was used to treat raw fabric for dye testing polyester jersey according to Example 7.

For each of the test fabrics treated as described in the preceding examples, the sterilization ratio, before washing and after a specified number of washings, was calculated using the shake-flask method.

Each consisted of washing in a domestic washing machine at a water temperature of 40 degrees Centigrade and a bath ratio of 1:30 for 5 minutes using 0.5 g Nissan Nonion NS-210 made by Nippon Yushi Kabushiki Kaisha as the detergent for each 1 L of water. Rinsing was carried out for 5 minutes.

The shake-flask method quantitatively measures antimicrobial activity by generating conditions approximating the actual conditions prevailing between the skin and bacteria by forcibly contacting the test fabric and bacteria. The following steps (1) through (6) were carried out.

(1) A 0.75 g piece of test sample of microbially treated fiber or raw fabric is taken as the test specimen.

(2) 70 mL sterile phosphate buffer is placed in a 200 mL Erlenmeyer flask, and inoculated with 5 mL of a bacterial liquid containing *Klebsiella pneumoniae* ATCC 4352 at $1.5 \times 10^5$ to $3 \times 10^5$ organisms/mL.

(3) 1 mL bacterial liquid is withdrawn from the Erlenmeyer flask and transferred to a test tube containing 9 mL sterile phosphate buffer, and mixed to homogeneity. 1 mL of mixture is withdrawn and diluted and mixed with 9 mL sterile phosphate buffer, and 1 mL re-diluted bacterial solution is withdrawn, placed in a sterile Petri dish, and fixed by the addition of 16 to 20 mL tryptone glucose extract agar culture medium. This is cultured at 37 degrees Centigrade for 18 to 24 hours.

(4) The test specimen from step (1) is placed in the Erlenmeyer flask described in step (2), and shaken for 1 hour using a wrist-action shaker. Again as in step (3), bacterial solution from the Erlenmeyer flask is transferred to a Petri dish, directly or after dilution mixing with sterile phosphate buffer, the medium is added, and cultured.

(5) In each of steps (3) and (4), a bacterial count is taken after culture, and the sterilization ratio is calculated as follows:

sterilization ratio (%) =

$$\frac{\text{(viable count for control)} - \text{(viable count for the processed specimen)}}{\text{(viable count for control)}} \times 100$$

(6) The same fiber or raw fabric, without the antimicrobial treatment, is also tested as above.

The results are reported in Table 1.

As the results in Table 1 indicate, the antimicrobial agent of the present invention has both a high antimicrobial activity as well as good resistance to washing.

TABLE 1

| Examples | Fabric Treated | Antimicrobial Agent | Sterilization Ratio (%) Number of Washes | | |
|---|---|---|---|---|---|
| | | | 0 | 10 | 20 |
| Example 7 | C-jersey | antimicrobial agent 1 | 100 | 99.8 | 91.0 |
| | C-jersey | antimicrobial agent 4 | 100 | 99.9 | 99.8 |
| | C-jersey | antimicrobial agent 6 | 100 | 99.6 | 99.6 |
| Example 8 | C-jersey | antimicrobial agent 2 | 100 | 99.8 | 99.8 |
| | C-jersey | antimicrobial agnet 5 | 100 | 98.0 | 87.6 |
| Example 9 | C-jersey | LDAEG | 100 | 49.0 | 22.0 |
| Example 10 | C-jersey | antimicrobial agent 3 | 100 | 99.2 | 80.0 |
| Example 11 | C-jersey | antimicrobial agent 3 | 100 | 99.9 | 99.4 |
| Example 12 | P-jersey | antimicrobial agent 3 | 100 | 97.0 | 94.0 |
| | P-jersey | antimicrobial agent 4 | 100 | 99.0 | 97.0 |
| Example 13 | P-jersey LDAEG | | 100 | 65.0 | 32.0 |

In the table, C = cotton, P = polyester, and LDAEG = lauryldi(aminoethyl)glycine.

That which is claimed is:

1. An antimicrobial agent wherein the compound is selected from the group consisting of compounds of the following formulas:

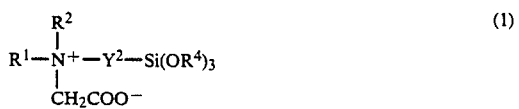

(1)

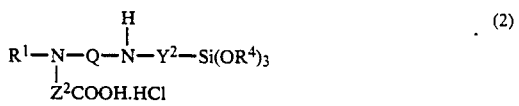

(2)

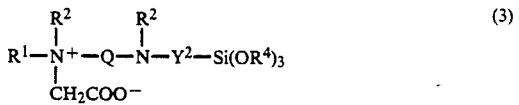

(3)

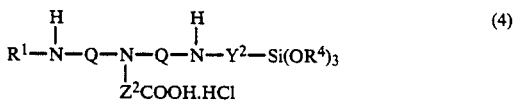

(4)

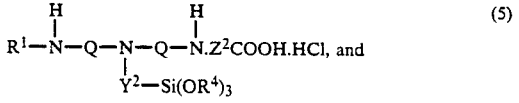

(5)

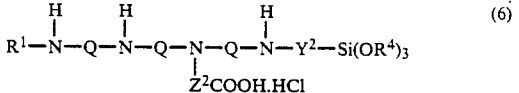

(6)

where Q is an alkylene group of 1 to 7 carbon atoms or the phenylene group; $Y^2$ is a divalent hydrocarbon radical of 1 to 8 carbon atoms or a radical of 1 to 8 carbon atoms which includes —COO— or —O— radicals; $Z^2$ is an alkylene radical; $R^1$ is a hydrophobic monovalent hydrocarbon group and $R^4$ is an alkyl or acyl group.

2. The compound of claim 1 wherein Q is —CH$_2$CH$_2$— or —CH$_2$CH$_2$CH$_2$—, $Y^2$ is selected from the group consisting of radicals of the following formulas:

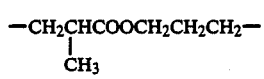

and

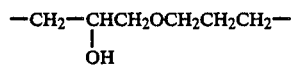

and $Z^2$ is

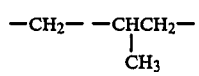

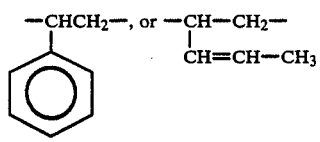

3. The compound of claim 1 where the nitrogen atom present in the molecule forms a salt with hydrogen halides.

4. The compound

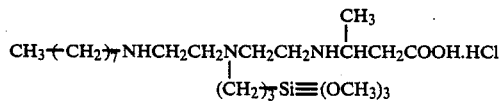

5. The compound

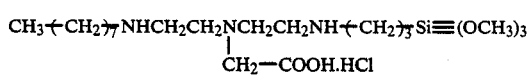

6. The compound

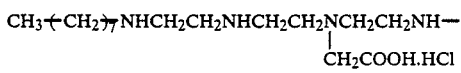

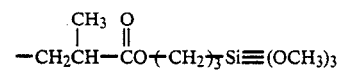

7. The compound

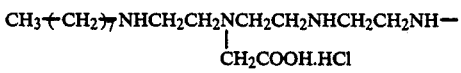

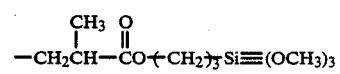

8. The compound

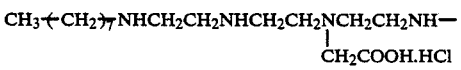

9. The compound

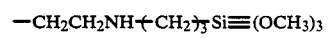

10. The compound

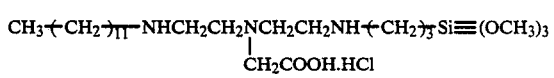

11. The compound

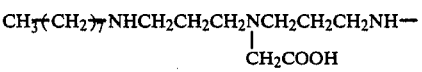

* * * * *